US010828045B1

(12) United States Patent
Zada (10) Patent No.: US 10,828,045 B1
(45) Date of Patent: Nov. 10, 2020

(54) TOURNIQUET DEVICE (71) Applicant: Avraham Zada, Hod Hasharon (IL)

(72) Inventor: Avraham Zada, Hod Hasharon (IL)

( * ) Notice: Subject to any disclaimer, the term of this patent is extended or adjusted under 35 U.S.C. 154(b) by 0 days.

(21) Appl. No.: 16/798,513

(22) Filed: Feb. 24, 2020

(51) Int. Cl.
*A61B 17/132* (2006.01)
*A61B 17/135* (2006.01)
*A61B 17/00* (2006.01)

(52) U.S. Cl.
CPC ........ *A61B 17/1325* (2013.01); *A61B 17/135* (2013.01); *A61B 2017/00548* (2013.01)

(58) Field of Classification Search
CPC ... A61B 5/022; A61B 5/02233; A61B 17/132; A61B 17/1322; A61B 17/1325; A61B 17/1327; A61B 17/135; A61B 17/1355
See application file for complete search history.

(56) References Cited

U.S. PATENT DOCUMENTS

| 2004/0122463 A1* | 6/2004 | Hibler | A61M 29/02 606/191 |
| 2012/0221041 A1* | 8/2012 | Hansson | A61B 17/135 606/203 |
| 2016/0038154 A1* | 2/2016 | Cohen | A61B 17/135 606/202 |
| 2019/0069905 A1* | 3/2019 | Pancholy | A61B 17/135 |
| 2020/0121546 A1* | 4/2020 | Theriot | A61H 9/0092 |

* cited by examiner

*Primary Examiner* — Ashley L Fishback
(74) *Attorney, Agent, or Firm* — Alphapatent Associates, Ltd; Daniel J. Swirsky (57) ABSTRACT

A device to apply pressure to a body tissue of a body part in order to limit the flow of blood in the body tissue, the device having an inflatable elastic layer having an internal side and an external side, the internal side configured to be in proximity to the body tissue, a rigid layer attached to the external side of the elastic layer limits an inflation direction of the elastic layer towards the body tissue, an inlet provided through a hole in the rigid layer or the elastic layer, a source of filling material connectable to the inlet to provide filling material into the elastic layer, where the source of filling material may be provided from a filling material container.

12 Claims, 8 Drawing Sheets

TOURNIQUET DEVICE

FIELD

The present invention is generally in the field of medical devices and in particular to a device which is attachable and reattach-able to a body tissue of a body part such as a limb, extremity or torso in order to limit the flow of blood in the body tissue.

BACKGROUND

A tourniquet is a device which applies pressure to a body tissue of a body part such as a limb, extremity or torso in order to limit the flow of blood in the body tissue to where damage to the body tissue is located. It may be used in emergency events such as car accidents and combats, in surgery, or in post-operative rehabilitation. A simple tourniquet can be made from a stick and a rope, or an elastic rope made for example of rubber or leather. The rope is made into a loop that fits over the damaged limb, and the stick is inserted through the loop. The loop is tightened by twisting the stick. The tightened loop may stem the flow of blood, but side-effects such as soft tissue damage and nerve damage may occur to the body tissue if the tightened loop is too tight or the tourniquet stays on the body tissue too long.

In addition, such tourniquets require significant time in order to press against the patient's tissue, for example 1-2 minutes per patient. Such long period of time may result in loss of blood and risk the patient's life. In addition, when there is a limited amount of medics or nurses relative to the number of injured persons, for example in a military unit or in a multi-injured accident, the medic is expected to place the tourniquet for multiple patients and hence there is a need for a tourniquet that can be installed to prevent blood flow within seconds, preferably 10-20 seconds.

SUMMARY

The subject matter discloses a device to apply pressure to a body tissue of a body part in order to limit the flow of blood in the body tissue. The device may be defined as a tourniquet. The device comprises an elastic layer and a rigid layer. The layers may be connected via a hole that enables passage of gas between the layers. The elastic layer is inflatable, and having an internal side and an external side, the internal side is configured to be in proximity to the body tissue. The rigid layer is attached to the external side of the elastic layer, thereby limits an inflation direction of the elastic layer towards the body tissue. An inlet is provided through a hole in the rigid layer and in the external side of the elastic layer. A source of filling material is connectable to the inlet to provide gas into the elastic layer via a hole in the rigid layer or a hole in the elastic layer. The source of filling material may be a container. The filling material container, or another container of gas, may be equipped with an activation module for activating the filling material container. The activation module may be a button, knob, switch and the like. In some cases, filling material is emitted from the filling material container upon maneuvering of the activation module. In some other cases, the activation module may be a sensor that senses that a connector of the filling material container is secured to the air inlet, for example using a screw or vacuum.

The body tissue onto which the device is pressed may be an arm, a leg or a torso. The body tissue may be a limb, the device may be attached to the limb, for example surrounding the entire cross section of the limb. The elastic layer may be inflated by the filling material after surrounding the entire cross section of the limb. The inflated layer provides a pressure between the limb and the rigid layer to enable the pressure to be applied to a surface area of the limb.

The cross-sectional shape of the rigid layer may be substantially that of the cross-sectional shape of the limb, for example a ring-like shape. The elastic layer inflated by the filling material provides a pressure to a surface area of the limb. The pressure may be applied between the limb and the rigid layer perpendicular to a normal of the surface area of the limb.

The elastic layer may be made of a polyvinyl chloride (PVC) coated with vinyl fabric. The elastic layer and the rigid layer may be assembled as an adjustable strap configured to wrap and attach around the limb.

The device may further comprise a rigid body insertable between the elastic layer and the body tissue. The inflated elastic layer may provide a compressive pressure to a surface area of the limb responsive to a shape factor of the rigid body between the limb and the rigid layer perpendicular to a normal of a surface area of the limb. The elastic layer and the rigid layer may be re-attachable to the limb. The elastic layer and the rigid layer may be foldable. The rigid layer may cover the entire external side of the elastic layer. The device may be a foldable strap, and may further comprise a connector for securing both ends of the strap.

The subject matter also discloses a kit formed by the device disclosed above and a container of filling material. The elastic layer and the rigid layer may be foldable around the body of the container of filling material and packed together.

BRIEF DESCRIPTION OF THE DRAWINGS

In order to understand the invention and to see how it may be carried out in practice, embodiments will now be described, by way of non-limiting example only, with reference to the accompanying drawings. Features shown in the drawings are meant to be illustrative of only some embodiments of the invention, unless otherwise implicitly indicated. In the drawings like reference numerals are used to indicate corresponding parts, and in which.

DETAILED DESCRIPTION

One or more specific embodiments of the present disclosure will be described below with reference to the drawings, which are to be considered in all aspects as illustrative only and not restrictive in any manner. In an effort to provide a concise description of these embodiments, not all features of an actual implementation are described in the specification. Elements illustrated in the drawings are not necessarily to scale, emphasis instead being placed upon clearly illustrating the principles of the invention. This invention may be provided in other specific forms and embodiments without departing from the essential characteristics described herein.

By way of introduction, the subject matter discloses an inflatable device which performs the function of a tourniquet. The device may be placed against a body part of a person in order to apply a pressure to the body tissue to limit the blood flow of in the body tissue. Specifically, the device of the subject matter applies the pressure to a surface area of the body part. The device comprises an elastic layer coupled to a rigid layer. The pressure is applied by inflating the elastic layer. The elastic layer is the part of the device located between the surface area of the body tissue and the rigid layer. The rigid layer forces the inflation direction of the elastic layer towards the body tissue. The inflation of the elastic layer is performed by emitting filling material via an aperture in the rigid layer from a source of pressurized gas.

Figure 1:
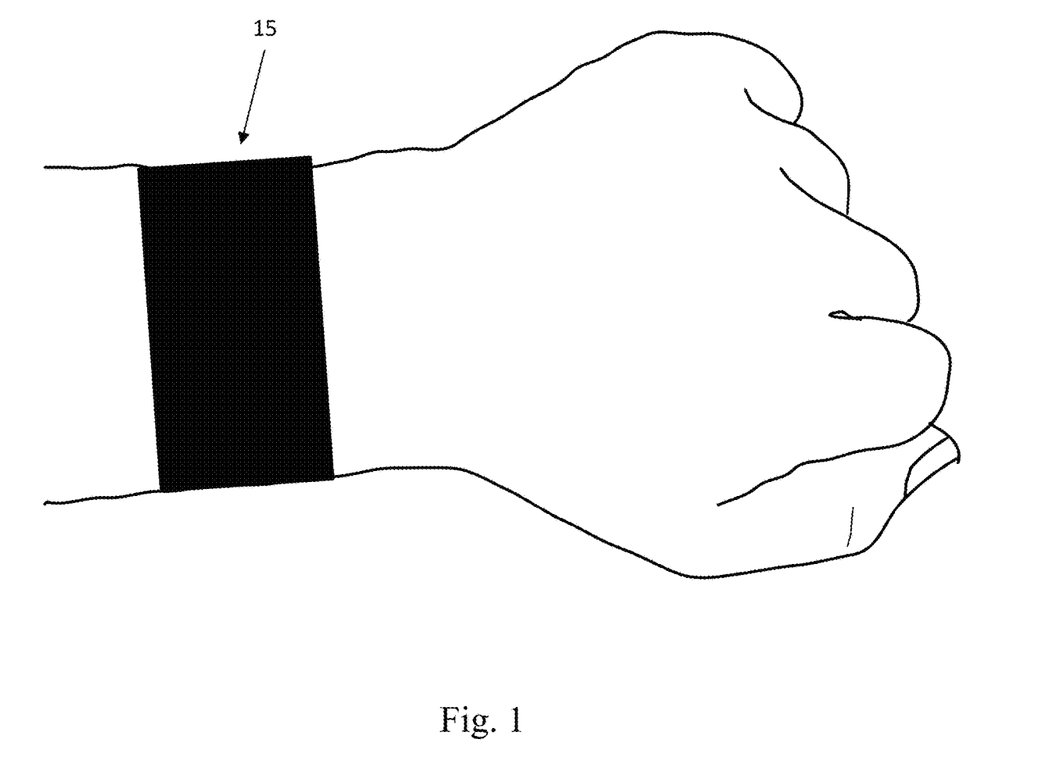
FIG. 1 shows a device applied to a body part of a person, according to one or more illustrative aspects of the disclosure.

Reference is now made to FIG. 1, which shows a device applied to a body part of a person, according to one or more illustrative aspects of the disclosure. Device 15 is shown surrounding the entire cross section of the user's arm. In some other cases, the body part onto which the device 15 is pressed may also be another limb such as a leg. The body part may be an extremity of the body such as finger or a toe. The body part may also be the torso of the body so that a pressure may be applied to the abdomen of the torso.

Figure 2A:
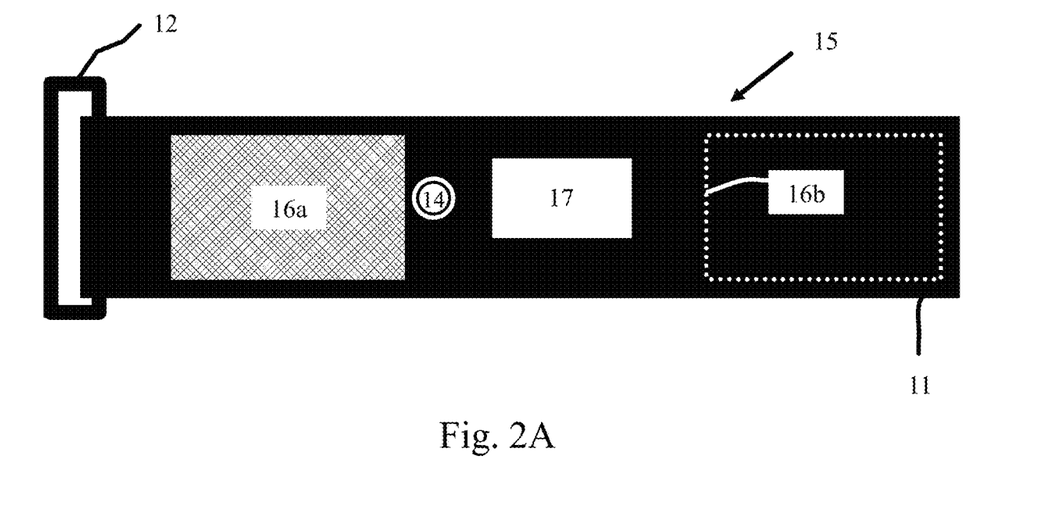
FIG. 2A shows a top view of a device to apply pressure to a body tissue having a filling material container secured to the rigid layer, said device is shaped as a strap, according to one or more illustrative aspects of the disclosure.

FIG. 2A shows a top view of a device to apply pressure to a body tissue having a filling material container secured to the rigid layer, said device is shaped as a strap, according to one or more illustrative aspects of the disclosure. The top view shows an adjustable strap implementation of device 15.

The top view of the device 15 shows a rigid layer 11 which at one distal end includes a buckle 12 and a hook patch 16a located on the upper outer surface of rigid layer 11. At the other end of the rigid layer 11 is a second loop patch 16b. Each of the loop patches 16a, 16b may be other connectors such as buttons and holes, magnetic-based connectors and the like. The connectors may be located on the under surface of rigid layer 11. The rigid layer 11 also comprises an inlet valve 14 located next to filling material container 17. Gas, for example air, flows from the filling material container 17 via the inlet valve 14 into the rigid layer 11, and via a hole inside the rigid layer to the elastic layer 13.

Figure 2B:
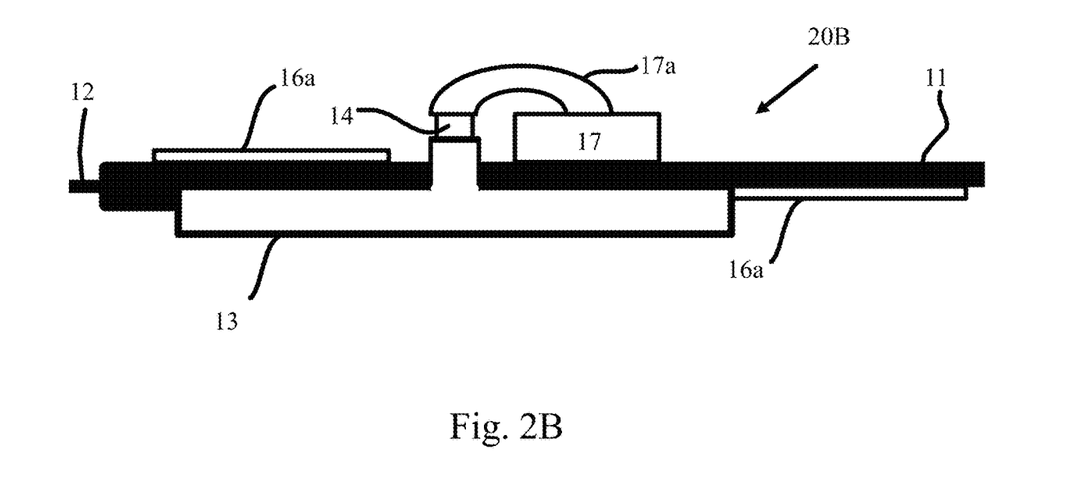
FIG. 2B shows a side view of a device to apply pressure to a body tissue having a filling material container secured to the rigid layer, said device is shaped as a strap, according to one or more illustrative aspects of the disclosure.

FIG. 2B shows a side view of a device to apply pressure to a body tissue having a filling material container secured to the rigid layer, said device is shaped as a strap, according to one or more illustrative aspects of the disclosure. The side view shows an elastic layer 13 is attached to the bottom surface of rigid layer 11, said bottom surface is a portion of the rigid layer 11 located closer to the user's body. In some exemplary cases, the elastic layer 13 is attached to the bottom surface of rigid layer 11 along the entire length of the elastic layer 13. In some other cases, the elastic layer 13 is attached to the bottom surface of rigid layer 11 along a portion of the length of the elastic layer 13. The elastic layer 13 has a hole configured to allow passage of filling material from the rigid layer. The rigid layer 11 has a void volume enabling gas to flow from the inlet valve 14 to the hole in the elastic layer 13, thereby inflating the elastic layer 13. The void volume of the rigid layer 11 is in fluid communication with the hold of the elastic layer. Elastic layer 13 may be polyvinyl chloride (PVC) coated vinyl fabric.

The side view of the device 15 shows air tube 17a connecting the output of filling material container 17 and inlet valve 14 to enable elastic layer 13 to be inflated and deflated through the aperture in rigid layer 11. The filling material container 17 may be secured to an external surface of the rigid layer 11, for example via adhesives, a strap or any other connector.

Figure 2C:
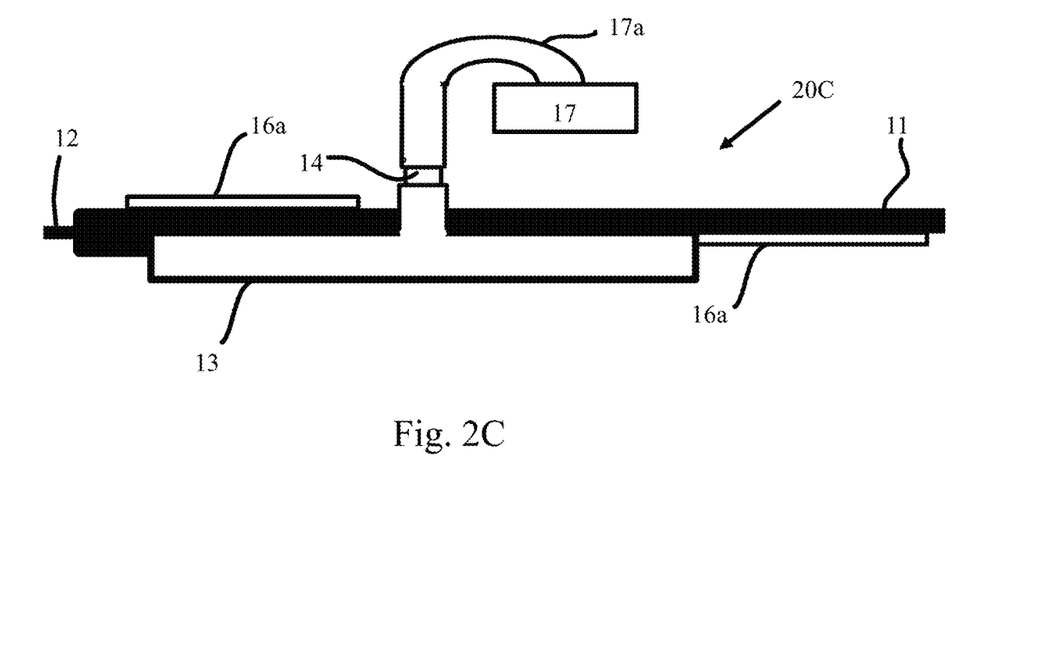
FIG. 2C shows a side view of a device to apply pressure to a body tissue having a filling material container located remotely from the rigid layer, said device is shaped as a strap, according to one or more illustrative aspects of the disclosure.

FIG. 2C shows a side view of a device to apply pressure to a body tissue having a filling material container located remotely from the rigid layer, said device is shaped as a strap, according to one or more illustrative aspects of the disclosure. The side view shows an exemplary embodiment in which the filling material container 17 is detached from rigid layer 11, located remotely from the rigid layer 11. A further option with respect to side views 22B and 22C is to provide a fastening on rigid layer 11 so that the filling material container 17 is both attachable and re-attachable to rigid layer 11. A pressure sensor may be located in line between filling material container 17 and inlet valve 14 to indicate to user the gas pressure in the elastic layer 13.

Figure 2D:
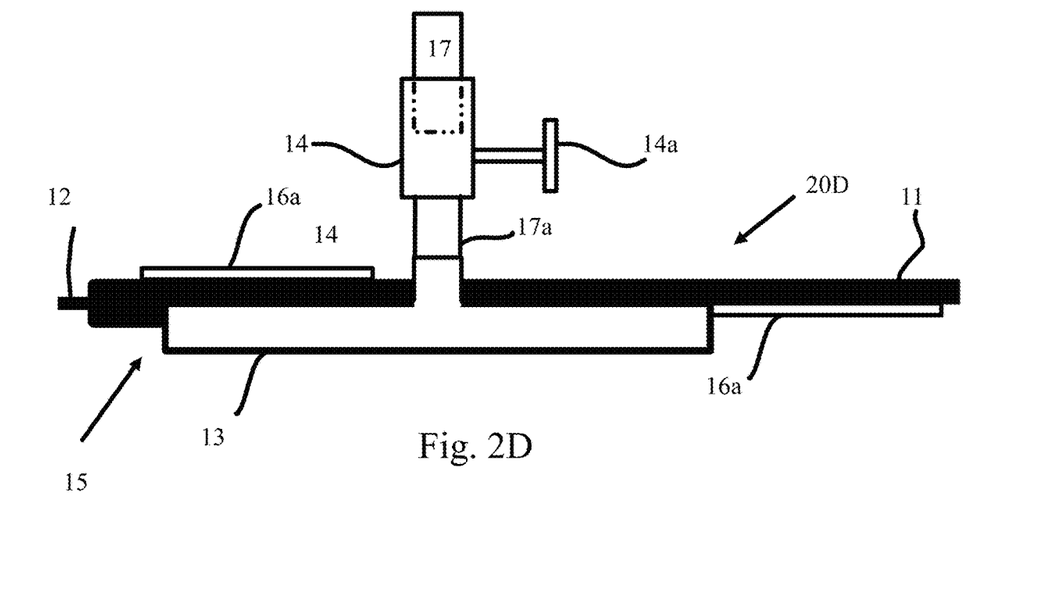
FIG. 2D shows a side view of a device to apply pressure to a body tissue having a filling material container is inserted into the inlet valve, according to one or more illustrative aspects of the disclosure.

FIG. 2D shows a side view of a device to apply pressure to a body tissue having a filling material container is connected into the inlet valve, according to one or more illustrative aspects of the disclosure. The filling material container 17 is coupled to a gas tube 17a configured to transfer the gas to the inlet valve 14. The gas tube 17a may be inserted into a body of inlet valve 14, or otherwise secured to the inlet valve in a manner that at least the majority of the air carried by the gas tube 17a is emitted into the inlet valve 14 and into the rigid layer 11. The coupling of the gas tube 17a with the inlet valve connects the filling material container 17 to inlet valve 14, such that gas flows via inlet valve to inflate the elastic layer 13 through the aperture in rigid layer 11. An activation module, such as handle 14a of inlet valve 14 may be used to regulate the inflation and/or deflation of elastic layer 13. Inlet valve 14 may also include a pressure gauge and/or pressure sensor located in line between filling material container 17 and valve 14 to indicate to user the pressure in elastic layer 13.

Figure 3A:
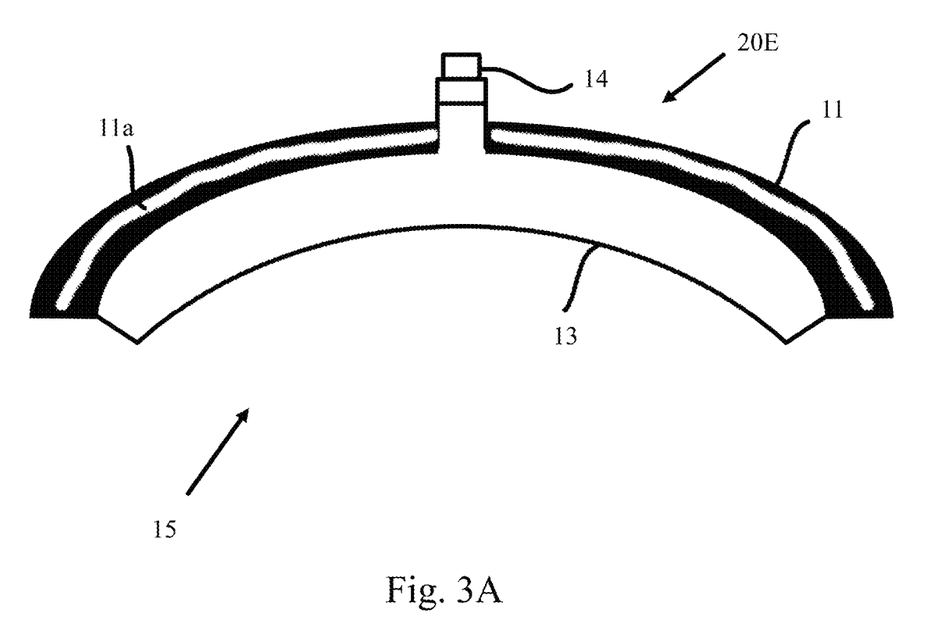
FIG. 3A shows a side view of a device having a mesh embedded into the rigid layer, according to one or more illustrative aspects of the disclosure.

FIG. 3A shows a side view of a device having a mesh embedded into the rigid layer, according to one or more illustrative aspects of the disclosure. Elastic layer 13 is shown attached to the bottom surface of rigid layer 11. A void volume in the rigid layer 11 is in fluid communication with a hole in the elastic layer 13, thereby enabling the elastic layer 13 to be inflated and deflated. In some exemplary embodiments, the rigid layer 11 may be shaped in a curved profile designed to restrict lateral expansion of elastic layer 13 from the sides of rigid layer 11. The curved profile may include a mesh 11a embedded in rigid layer 11 during manufacture of the rigid layer 11. Mesh 11a may be made of nylon or a steel mesh or a composite mesh material which allows device 15 to be wrapped around a person's body part while preventing elastic stretch of rigid layer 11 when elastic layer 13 is inflated. Mesh 11a may be foldable so that it may be stored in a pocket of a garment or bag of a user of device 15. The material of rigid layer 11 may be a natural rubber, a synthetic rubber such as styrene-butadiene co-polymer, polybutadiene rubber or halobutyl rubber.

The elastic layer inflates by at least 50 percent relative to the deflated status. In some other cases, the range of inflation of the elastic layer may be 2-30 times the volume of the elastic layer in the deflated state. When the elastic layer is inflated in response to emitting gas therein, the amount of gas in the gas container may be in the range of 3-150 grams. In some exemplary cases, a single container can be used to fill multiple devices.

Figure 3B:
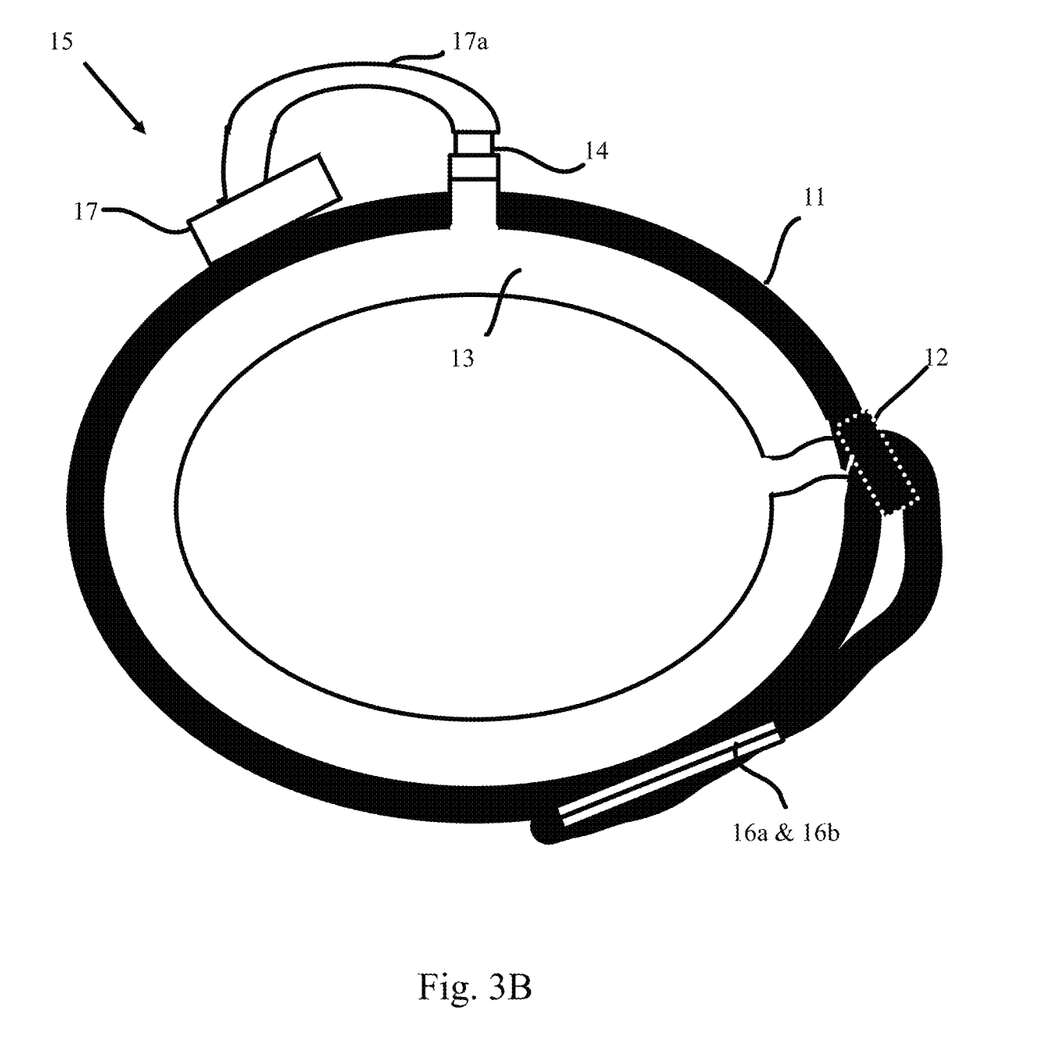
FIG. 3B shows a side view of a device that uses hooks and loops to secure both ends of the strap around the patient's limb, according to one or more illustrative aspects of the disclosure.

FIG. 3B shows a side view of a device that uses hooks and loops to secure both ends of the strap around the patient's limb, according to one or more illustrative aspects of the disclosure. The adjustable strap implementation of device 15 is shown where buckle 12 is utilized to fasten the two distal ends of rigid body 11 together by attaching hooks and loops patch 16a located on the upper outer surface of rigid layer 11 to hooks and loops patch 16b located on the under surface of rigid layer 11. Other connectors may replace the hooks and loops, for example metal connectors, magnetic connectors, straps, buttons and the like. FIG. 3B shows a state in which the elastic layer 13 is deflated and filling material container 17 is secured to the upper surface of rigid layer 11. Gas tube 17a connects container 17 to inlet valve 14. Elastic layer 13 is attached to the bottom surface of rigid layer 11 and air flows from the inlet valve 14 through an aperture in rigid layer 11 to the elastic layer 13 to be inflated or deflated. Instead of buckle 12, Velcro™ hook patch 16a and Velcro™ loop patch 16b, a double 'D-ring' may be used to attach the two distal ends of rigid body 11 together.

Figure 3C:
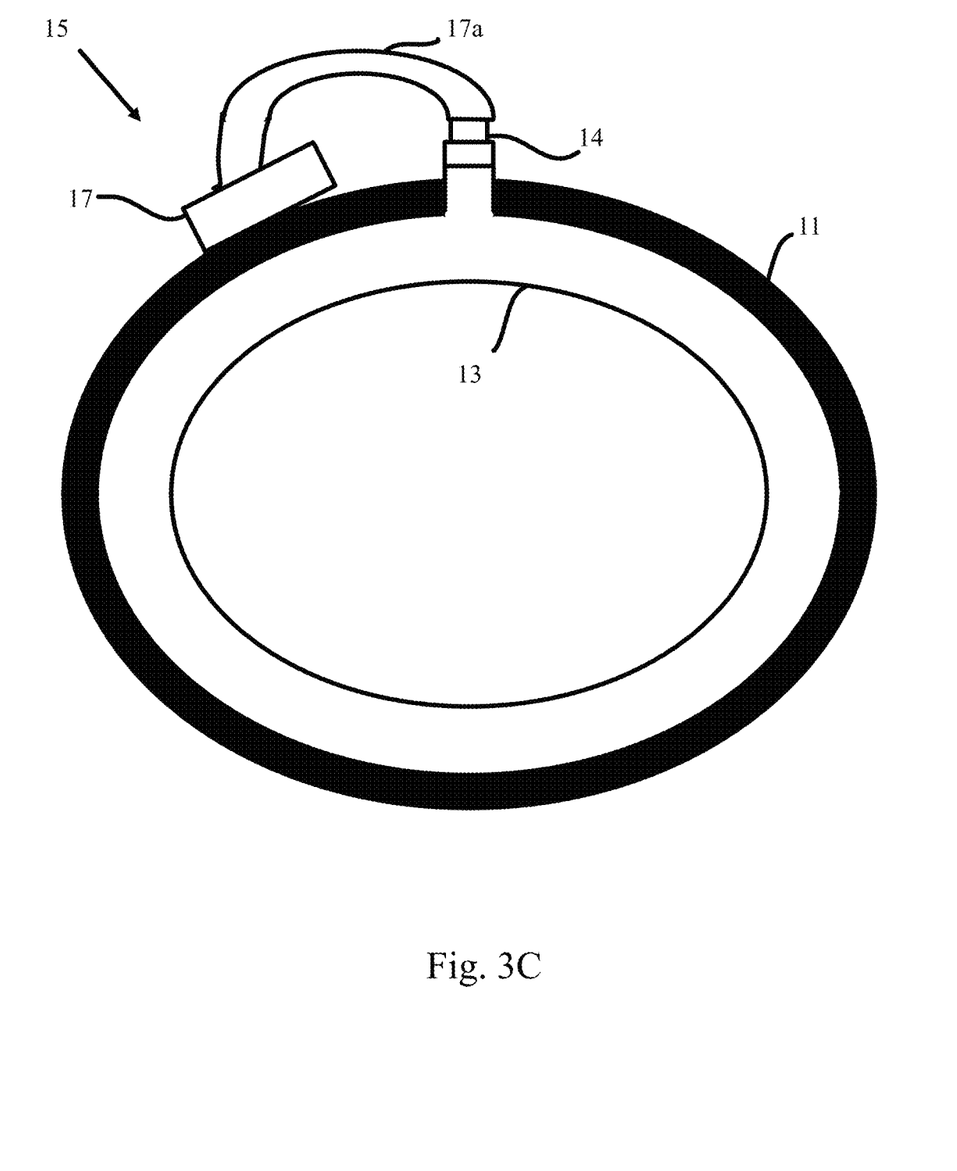
FIG. 3C shows a side view of a device having the rigid layer in a ring shape, according to one or more illustrative aspects of the disclosure.

FIG. 3C shows a side view of a device having the rigid layer in a ring shape, according to one or more illustrative aspects of the disclosure. The side view shows a bracelet arrangement for device 15 which may have an appropriate circumference size to make the bracelet surround a torso, an arm or a leg when elastic layer 13 is in a deflated state. Elastic layer 13 is attached to the bottom surface of rigid layer 11 and protrudes through an aperture in rigid layer 11 to enable elastic layer 13 to be inflated or deflated.

Figure 4A:
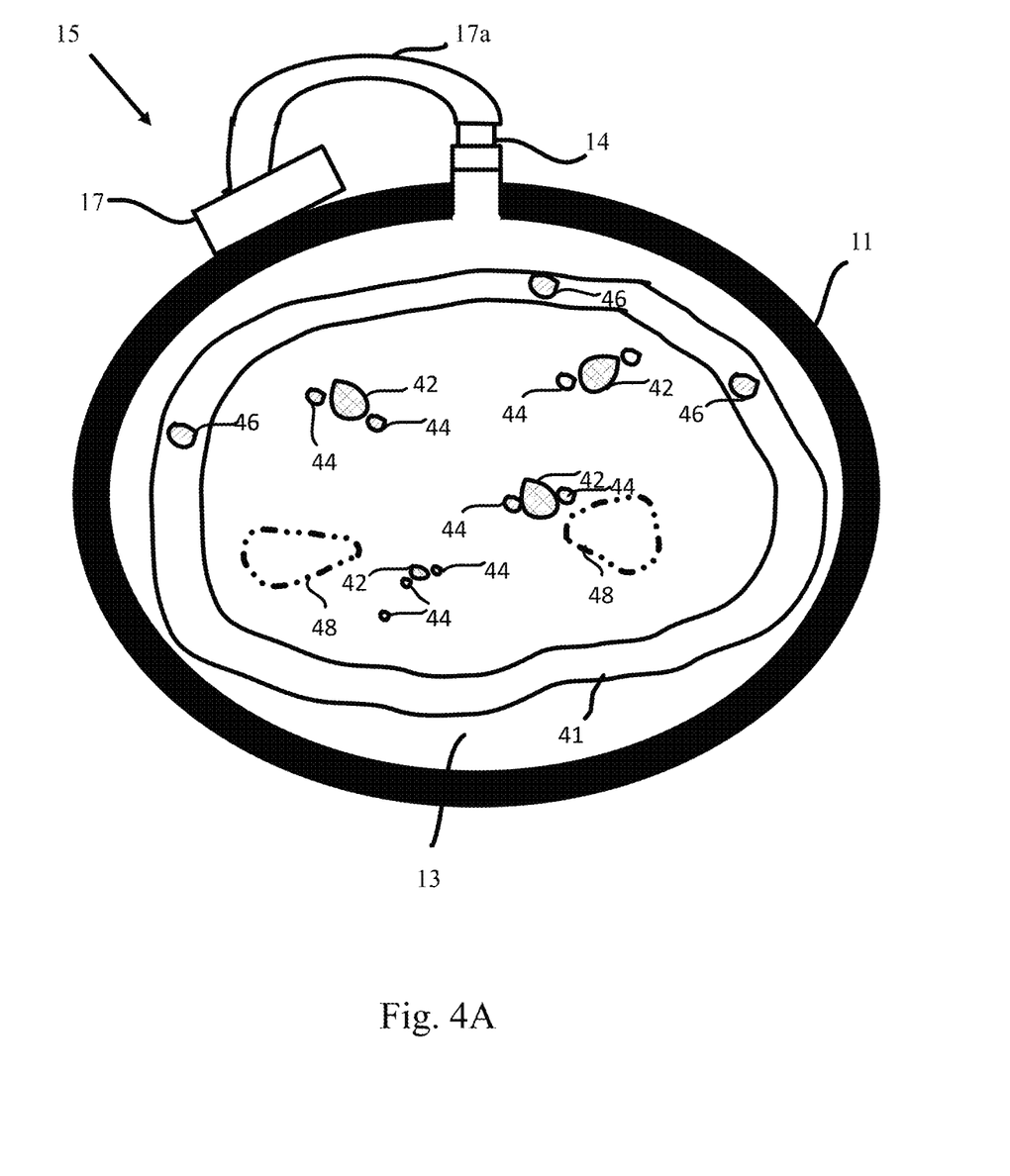
FIG. 4A shows a side view of a device and cross section of a body part, according to one or more illustrative aspects of the disclosure.

Reference is now made to FIG. 4A, which shows a side view of device 15 and cross section of a body part, according to one or more illustrative aspects of the disclosure. The side view shows a ring-shaped arrangement of the device 15 and may also function when designed as an adjustable strap as shown above. By way of a non-limiting example, device 15 is shown surrounding a body part such as a limb when elastic layer 13 is in inflated state. The cross-sectional shape of the rigid layer 11 is substantially that of the cross-sectional shape of the limb. Elastic layer 13 is inflated by the filling material emitted from the container 17. The filling material of filling material container 17 is delivered to elastic layer 13 through tube 17a and valve inlet 14. Inlet valve 14 transfers gas to elastic layer 13 through the aperture in rigid layer 11. The filling material may be pressurized gas, expendable foam, liquid and the like.

Inflation of elastic layer 13 applies a pressure to a surface area of the limb. The surface area being that of the length and width of elastic layer 13 contained within the underside of rigid layer 11 as it encloses around the cross section of the limb. The pressure is built between the surface area of the limb and rigid layer 11. The pressure applied to the surface area may be perpendicular to a normal of the surface area. The pressure may be applied evenly to surface veins 46 in the epidermis 41, muscles, deep veins 44, arteries 42 and bones 48 of the limb. The pressure therefore limits the flow of blood in the limb.

Figure 4B:
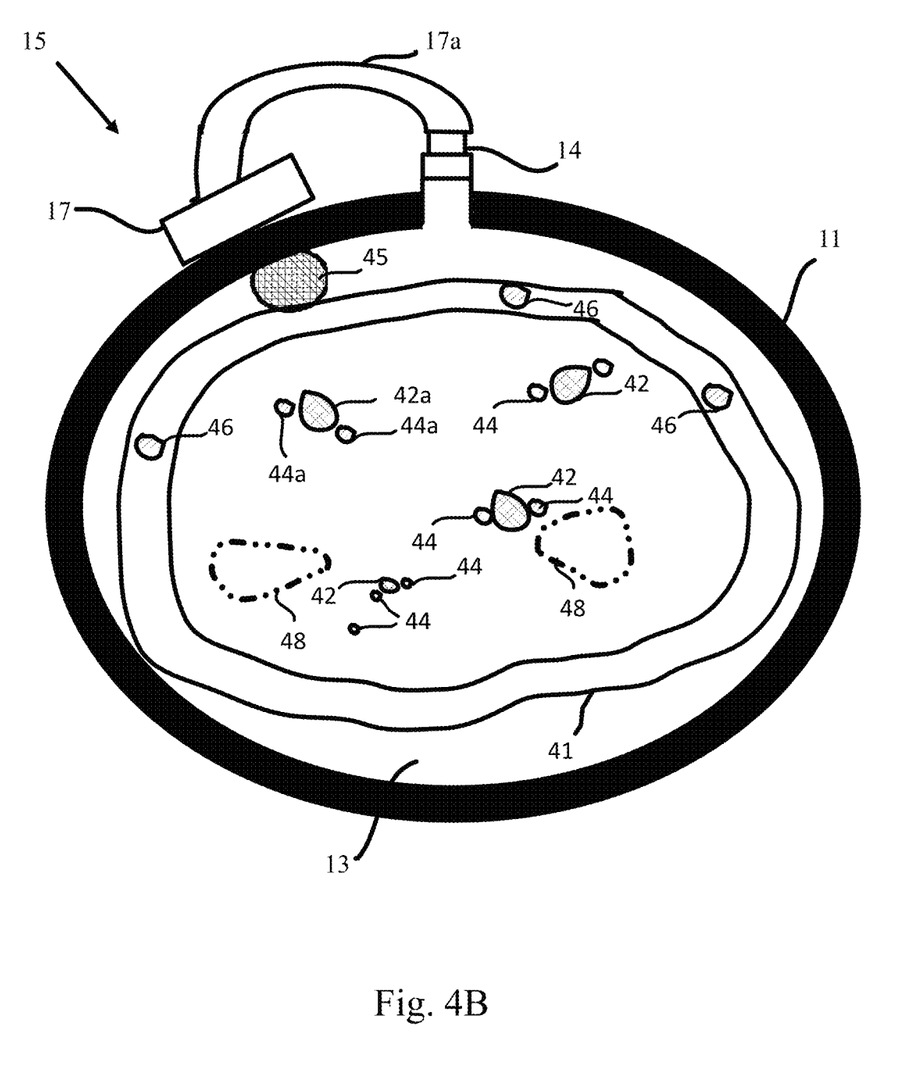
FIG. 4B shows a side view of a device and cross section of a body part, wherein a rigid body is placed between the limb and the rigid layer according to one or more illustrative aspects of the disclosure.

FIG. 4B shows a side view of a device and cross section of a body part, wherein a rigid body is placed between the limb and the rigid layer according to one or more illustrative aspects of the disclosure. The side view shows a rigid body 45 placed between the limb and the rigid layer 11, perpendicular to a normal of a surface area of the limb. Inflation of elastic layer 13 provides a pressure to a surface area of the limb. The surface area being substantially equal of the length and width of elastic layer 13 attached at least partially to a bottom surface of rigid layer 11 as it surrounds the cross section of the limb. The pressure is generated between the surface area of the limb and rigid layer 11. The pressure applied to the surface area may be perpendicular to a normal of the surface area. The pressure may be evenly to surface veins 46 in the epidermis 41, muscles, deep veins 44, arteries 42 and bones 48 of the limb. The pressure therefore limits the flow of blood in the limb. Pressure (P), Force (F) and area (A) is given by the standard formula below:

$$P = \frac{F}{A}$$

The inclusion of rigid body 45 allows additional increased pressure (P) to be applied to deep veins 44a and artery 42a responsive to a shape factor of rigid body 45 which provides a smaller area (A).

As described hereinabove and shown in the Figures, the present invention provides a device to enable to the application of pressure to a body tissue of a body part in order to limit the flow of blood through the tissue. While particular embodiments of the invention have been described, it will be understood, however, that the invention is not limited thereto, since modifications may be made by those skilled in the art, particularly in light of the foregoing teachings. As will be appreciated by the skilled person, the invention can be carried out in a great variety of ways, employing more than one technique from those described above, all without exceeding the scope of the invention.

What is claimed is:

1. A kit to apply pressure to a body tissue of a body part in order to limit the flow of blood, the kit comprising:
   a device configured to be pressed against a body part, said device comprising:
   an elastic layer configured to surround an entire cross section of the body part, wherein the elastic layer is inflatable, the elastic layer having an internal side and an external side, said internal side is configured to be in proximity to a body tissue;
   a rigid layer attached to the external side of the elastic layer, thereby limiting an inflation direction of the elastic layer towards the body tissue; and
   an inlet provided through a hole in the rigid layer or a hole in the elastic layer in order to provide filling material into the elastic layer;

a source of filling material configured to connect to the inlet to provide the filling material into the elastic layer.

2. The kit of claim 1, wherein the source of filling material comprises an activation module, wherein the filling material is emitted from the source of filling material in response to moving of the activation module.

3. The kit of claim 1, wherein the body tissue is a limb, wherein the device is configured to be attached to the limb and the elastic layer inflated by the source of filling material provides a pressure between the limb and the rigid layer to enable the pressure to be applied to a surface area of the limb.

4. The kit of claim 3, wherein a cross-sectional shape of the rigid layer is substantially that of the cross-sectional shape of the limb, wherein the elastic layer inflated by the source of filling material provides a pressure to a surface area of the limb, wherein the pressure is created between the limb and the rigid layer perpendicular to a normal of the surface area of the limb.

5. The kit of claim 3, wherein the elastic layer and the rigid layer form an adjustable strap configured to wrap and attach around the limb.

6. The kit of claim 5, further comprising a connector for adjusting the length of the strap and securing both ends of the strap.

7. The kit of claim 1, wherein the elastic layer is made of a polyvinyl chloride (PVC) coated with vinyl fabric.

8. The kit of claim 1, wherein the device is a foldable strap, wherein the elastic layer and the rigid layer are foldable around the source of filling material.

9. The kit of claim 1, wherein the rigid layer covers the entire external side of the elastic layer.

10. The kit of claim 1, wherein the body part is at least one of an arm, a leg and a torso.

11. The kit of claim 1, wherein the source of filling material is a gas container containing pressurized gas.

12. The kit of claim 1, wherein the source of filling material is a container containing expendable foam.

* * * * *